United States Patent [19]

Yabe et al.

[11] Patent Number: 5,419,311
[45] Date of Patent: May 30, 1995

[54] ENDOSCOPE APPARATUS OF A TYPE HAVING COVER FOR COVERING THE ENDOSCOPE

[75] Inventors: Hisao Yabe, Hachioji; Yoshihiro Iida, Tama; Akira Suzuki; Hideo Ito, both of Hachioji; Yoshio Tashiro, Hino; Minoru Yamazaki; Osamu Tamada, both of Hachioji; Yosuke Yoshimoto, Tama, all of Japan

[73] Assignee: Olympus Optical Co., Ltd., Tokyo, Japan

[21] Appl. No.: 28,142

[22] Filed: Mar. 9, 1993

[30] Foreign Application Priority Data

Feb. 18, 1993 [JP] Japan ................... 5-005245 U
Feb. 18, 1993 [JP] Japan ................... 5-005246 U

[51] Int. Cl.⁶ ............................................. A61B 1/00
[52] U.S. Cl. .................................................... 128/4
[58] Field of Search ....................... 128/4, 6, 9, 10; 206/459.5

[56] References Cited

U.S. PATENT DOCUMENTS

| | | | |
|---|---|---|---|
| 4,281,646 | 8/1981 | Kinoshita | 128/6 |
| 4,646,722 | 3/1987 | Silverstein et al. | 128/4 |
| 4,765,312 | 8/1988 | Sasa et al. | 128/4 |
| 4,878,485 | 11/1989 | Adair | 128/4 X |
| 4,974,580 | 12/1990 | Anapliotis | 128/4 |
| 5,072,833 | 12/1991 | Hansen et al. | 206/459.5 X |
| 5,105,800 | 4/1992 | Takahashi et al. | 128/4 |
| 5,167,235 | 12/1992 | Seacord et al. | 128/664 |
| 5,201,908 | 4/1993 | Jones | 128/4 |

*Primary Examiner*—Richard J. Apley
*Assistant Examiner*—Beverly A. Meindl
*Attorney, Agent, or Firm*—Armstrong, Westerman, Hattori, McLeland & Naughton

[57] ABSTRACT

An endoscope apparatus of a type having a cover for covering the endoscope composed of a cover for an insert, a cover for a control unit, and a universal-cord cover, and the endoscope which uses the endoscope cover to cover the control unit having a handle in the body of the control unit, an elongated insert extending from the control unit to the leading portion and a universal cord extending from the control unit. At least two members of all members that form the cover for the insert of the endoscope cover, for example, a leading unit and an acceptor for fixing the control unit of the endoscope, are made of the same material such as polysulfone which is a thermoplastic resin which can be recycled, or all members forming the cover for the insert are made of a material which can be subjected to a combustion process, or the cover for the control unit integrally covers the insert and the handle of the endoscope with the endoscope cover.

7 Claims, 17 Drawing Sheets

ENDOSCOPE APPARATUS OF A TYPE HAVING COVER FOR COVERING THE ENDOSCOPE

BACKGROUND OF THE INVENTION

1. Field of the Invention

The present invention relates to an endoscope apparatus of a type having a cover for covering the endoscope to prevent contamination of the endoscope.

2. Description of the Related Art

Endoscopes are widely used in the medical field and so forth. When an inspection with an endoscope of the type for use in the medical field is performed, a clean endoscope sufficiently must be used which is washed and disinfected prior to the inspection.

However, the endoscope usually has air-supply and water-supply passages and a forceps channel, requiring a long time to completely clean or disinfect the insides of the pipe portions. Since the disinfection process must be performed sufficiently to obtain a desired effect, the process must be performed for a long period of time. As a result, a problem arises in that the efficiency in using the endoscope deteriorates. Another problem is that the disinfection process is too complicated to be completed.

In view of overcoming the aforesaid problems, an endoscope apparatus of a type having a cover for covering the endoscope has been disclosed, in which the body of an endoscope is used in a state where it is covered with a cover for the endoscope, and only the cover for the endoscope is disposed of after use and replaced to prevent the unclean state of the body of the endoscope so that the the necessity of performing the cleaning operation and the disinfection process are eliminated. The foregoing structure has been disclosed in, for example, U.S. Pat. Nos. 5,050,585, 4,646,722, Europe Patent Application Laid-Open No. 0,341,719, Japanese Patent Publication No. 2-54734, and U.S. Pat. No. 3,162,190.

Specifically, the endoscope for use with the endoscope cover fastened is used in such a manner that its insert is previously cleaned and subjected to a sterilization and disinfecting process, and the insert and the like of the endoscope are covered with the endoscope cover followed by insertion of the insert into the coelom of a patient to inspect or cure the patient. After the endoscope has been used, the endoscope cover for covering the body of the endoscope is removed and disposed. By disposing the endoscope cover for each patient as described above, the body of the endoscope does not need to be cleaned or disinfected. Therefore, it can always be kept clean and sanitary. Since the body of the endoscope can be successively used while eliminating the necessity of cleaning and disinfecting it, the efficiency of using the endoscope can be satisfactorily improved.

Recently, there has arisen a problem of the disposition of the disposable products in view of environmental safeguards. Therefore, it is desirable that the manufacturer supplies products to consumers while taking, for example, recycling into consideration. However, the foregoing conventional endoscope covers have not been satisfactorily adaptable to the foregoing circumstance. Although the recycle must be so performed that the components are divided depending upon the material, the conventional endoscope cover incorporates components which are made of a multiplicity of materials, causing a problem to arise in that the division takes a too long time. In addition, the materials employed to constitute the members are not suitable to be subjected to the recycle process. The conventional endoscope cover sometimes employs an adhesive agent to connect the components, resulting in difficulty in decomposing the components. Furthermore, the adhesive agent usually contains a variety of components, resulting in a problem in that the components with the adhesive agent cannot be adaptable to the recycle process.

Furthermore, it is preferred in view of the environmental safeguards that the manufacturer considers the combustion facility when it supplies the disposable products to consumers. However, the conventional endoscope covers have not satisfactorily met the foregoing requirement. That is, the conventional endoscope cover has components that partially contain metals and resins. Therefore, there arises a problem at the combustion of the disposed components in that they cannot be subjected to the combustion process. The metals, which cannot be subjected to the combustion process, and resins, which can be subjected to the combustion process, must be divided to dispose them. Moreover, some resins for use in the conventional endoscope cover generate poisonous gas at the time of the combustion process. Therefore, some resin components cannot be subjected to the combustion process as it is. In addition, the conventional endoscope cover sometimes uses an adhesive agent to connect the components to each other, causing a difficulty to arise at the time of decomposing the components. Furthermore, the adhesive agent usually contains various components, causing a problem to arise in that poisonous gas sometimes is generated depending upon the type of the adhesive agent.

The endoscope cover of the conventional endoscope apparatus of a type having the endoscope cover disclosed in Europe Patent Publication Laid-Open No. 0,341,719 incorporates a cover for an insert of the endoscope and a cover for the control unit of the endoscope. The control unit of the endoscope has a handle in the leading portion and the cover for the control unit covers the portion including the handle. In the foregoing structure, the boundary between the cover for the control unit and the cover for the insert is positioned below the handle that can easily be contaminated. In the foregoing case, the invasion of contaminants through the boundary or that due to the undesirable shift of the cover for the control unit during use of the endoscope must be prevented by carefully fastening the cover. The portion covered with the cover for the insert of the conventional endoscope cover is provided with the forceps channel and the air/water-supply passages. If the structure is so arranged that the base of the cover for the insert is positioned more forwards than the handle, the passage outwards extending from the base of the cover for the insert is undesirably positioned below the handle. As a result, the foregoing passage interrupts the operation with the endoscope, causing deterioration to arise in the operation facility.

SUMMARY OF THE INVENTION

A first object of the present invention is to provide an endoscope apparatus of a type having a cover for covering the endoscope capable of easy decomposing and dividing the components depending upon the materials and accordingly adaptable to recycle.

A second object of the present invention is to provide an endoscope apparatus of a type having a cover for covering the endoscope that includes a cover for an insert that can be subjected to a combustion process as it is.

A third object of the present invention is to provide an endoscope apparatus of a type having a cover for covering the endoscope with which an excellent operation facility can be obtained and which is capable of preventing contamination through the boundary between a cover for a control unit and a cover for an insert while eliminating the necessity for strict attention.

A fourth object of the present invention is to provide an endoscope apparatus of a type having a cover for covering the endoscope that includes a cover for an insert, the members of which can be easily decomposed.

A fifth object of the present invention is to provide an endoscope apparatus of a type having a cover for covering the endoscope that includes a cover for an insert, the members of which can be easily divided.

A sixth object of the present invention is to provide an endoscope apparatus of a type having a cover for covering the endoscope that includes a cover for an insert, the members of which can easily be visually recognized and divided.

A seventh object of the present invention is to provide an endoscope apparatus of a type having a cover for covering the endoscope with which fluid does not drop from the passage at the time of removing the cover for the insert.

An eighth object of the present invention is to provide an endoscope apparatus of a type having a cover for covering the endoscope with which fluid does not drop from an opening in the leading portion of the passage at the time of removing the cover for the insert.

A ninth object of the present invention is to provide an endoscope apparatus of a type having a cover for covering the endoscope that includes a cover for an inset which can easily be assembled.

A tenth object of the present invention is to provide an endoscope apparatus of a type having a cover for covering the endoscope that includes a cover for an insert in which passages are not moved by pressure.

An eleventh object of the present invention is to provide an endoscope apparatus of a type having a cover for covering the endoscope capable of forwards supplying fluid from the leading portion of the endoscope.

A twelfth object of the present invention is to provide an endoscope apparatus of a type having a cover for covering the endoscope that includes fluid passages which do not deteriorate the operation facility.

A thirteenth object of the present invention is to provide an endoscope apparatus of a type having a cover for covering the endoscope that includes an angle-knob cover which can simply be fastened.

In brief, an endoscope apparatus of a type having a cover for covering the endoscope comprising: a cover for an insert incorporating two or more members that are made of the same material which can be recycled, or a cover for the insert made of materials which can be subjected to a combustion process, or a cover for the insert which is able to cover a handle of a control unit; a cover for the endoscope having a cover for the insert; and an endoscope using the cover for the endoscope to cover at least the surface of the insert.

These objects and advantage of the present invention will become further apparent from the following detailed explanation.

BRIEF DESCRIPTION OF THE DRAWINGS

FIG. 1 is a perspective view which illustrates the overall structure of an endoscope apparatus of a type having a cover for covering the endoscope;

FIG. 2 is a side elevational view which illustrates an endoscope with a cover;

FIG. 3 is a vertical cross sectional view which illustrates a cover for an insert in a state where it is fastened to the endoscope with the cover;

FIG. 4 is a vertical cross sectional view which illustrates a cover for an insert in a state where it is not fastened to the endoscope with the cover;

FIG. 5 is a vertical cross sectional view which illustrates a forceps cap to be fastened to an insertion port for the forceps at the time of use;

FIG. 9 is a vertical cross sectional view which illustrates a cover for the insert of the endoscope in a state where it is fastened to the endoscope with the cover;

FIG. 10 is a perspective view which illustrates a check valve;

FIG. 11 is a vertical cross sectional view which illustrates a cover for an insert of a cover for the endoscope in a state where it is fastened to an endoscope with an endoscope cover;

FIG. 12 is cross sectional view taken along line A—A of FIG. 11 which illustrates a multilumen tube in a state where the endoscope with the endoscope cover is not fastened;

FIG. 13 is a perspective view which illustrates a leading portion of an insert to which a cover for an insert is fastened;

FIG. 14 is a vertical cross sectional view which illustrates a cover for the insert of the endoscope in a state where it is fastened to the endoscope with the cover and in which a portion including the forward water-supply passage is shown;

FIG. 15 is a perspective view which illustrates the overall structure of an endoscope apparatus of a type having a cover for covering the endoscope;

FIG. 16 is a side elevational view which illustrates an endoscope with an endoscope cover and a cover for an insert of the endoscope cover;

FIG. 17 is a vertical cross sectional view which illustrates a cover for an insert of an endoscope cover in a state where it is fastened to the endoscope with the endoscope cover;

FIG. 18 is a perspective view which illustrates a state where the cover for a control unit and an angle knob are fastened after the cover for the insert is fastened to the endoscope with the endoscope cover;

FIG. 19 is a perspective view which illustrates an angle-knob cover;

FIG. 20 is a plan view including a partial cross sectional view which illustrates the cover for a control unit, an angle knob and a cover for the angle knob fastened to the body of the control unit;

FIG. 21 is a plan view including a partial cross sectional view which illustrates another example of the cover for the angle knob of the body of the control unit shown in FIG. 20.

DETAILED DESCRIPTION OF THE PREFERRED EMBODIMENTS

Preferred embodiments of the present invention will now be described with reference to the drawings.

Figure 1:
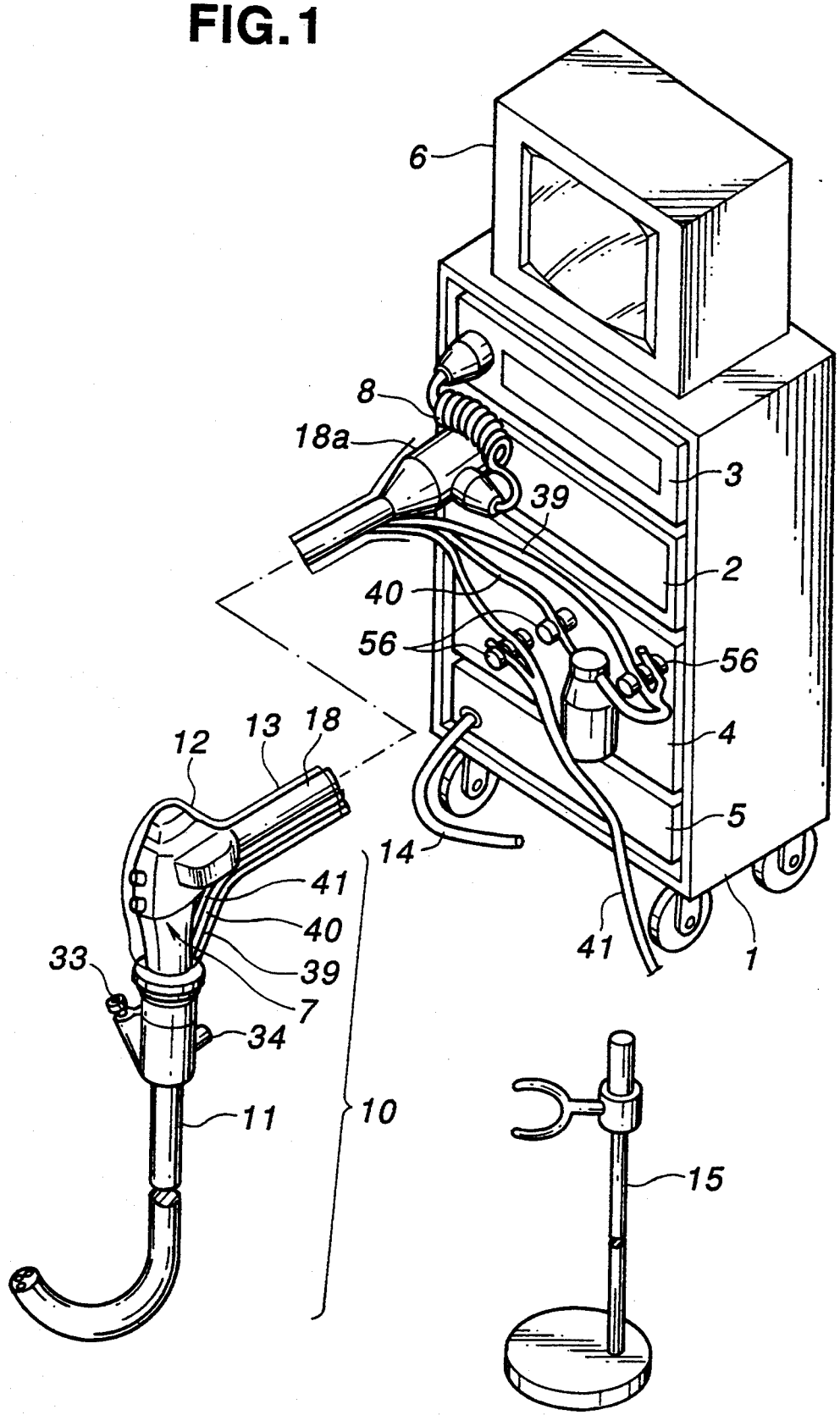
FIGS. 1 to 5 illustrate a first embodiment of the present invention, where
Figure 2:
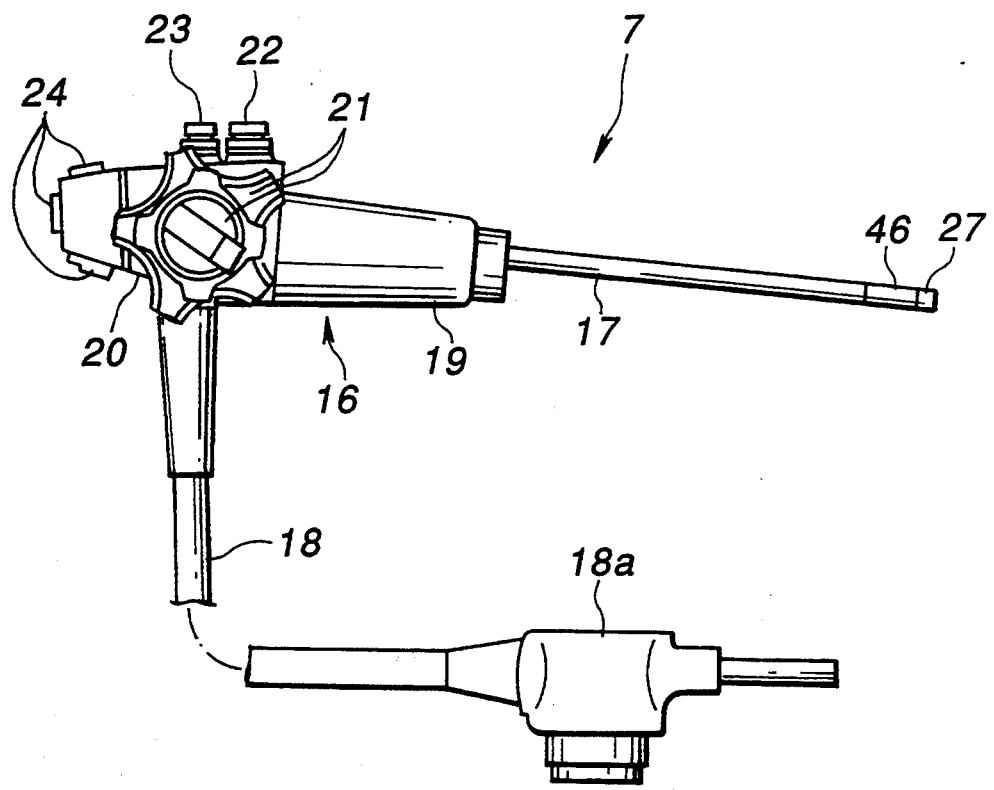
Figure 5:
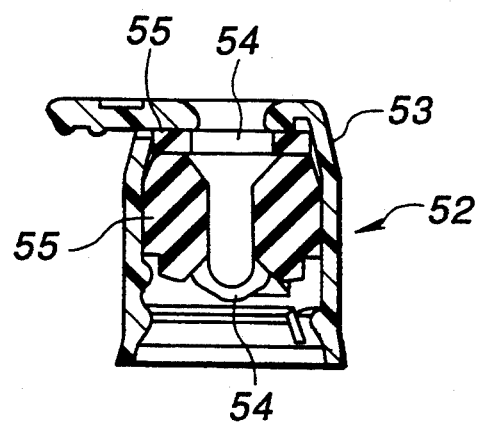
Figure 3:
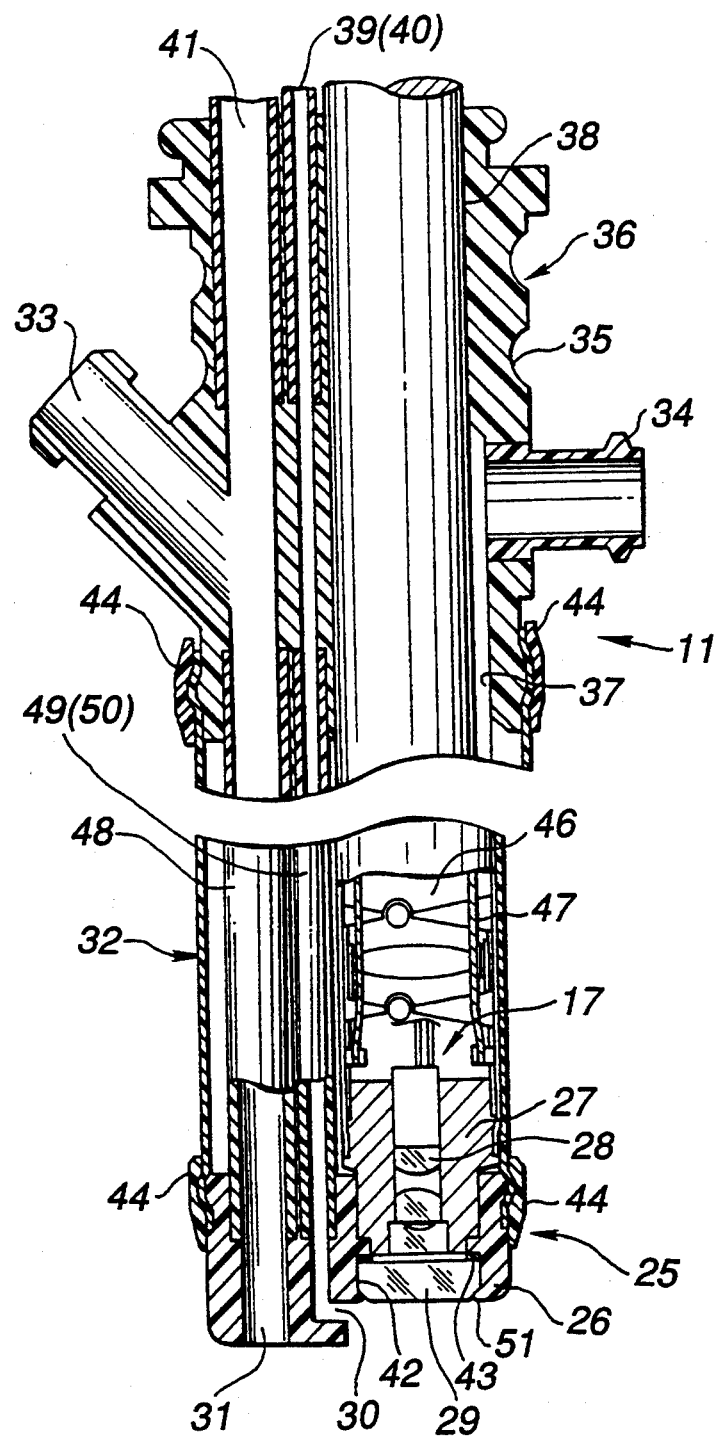
Figure 4:
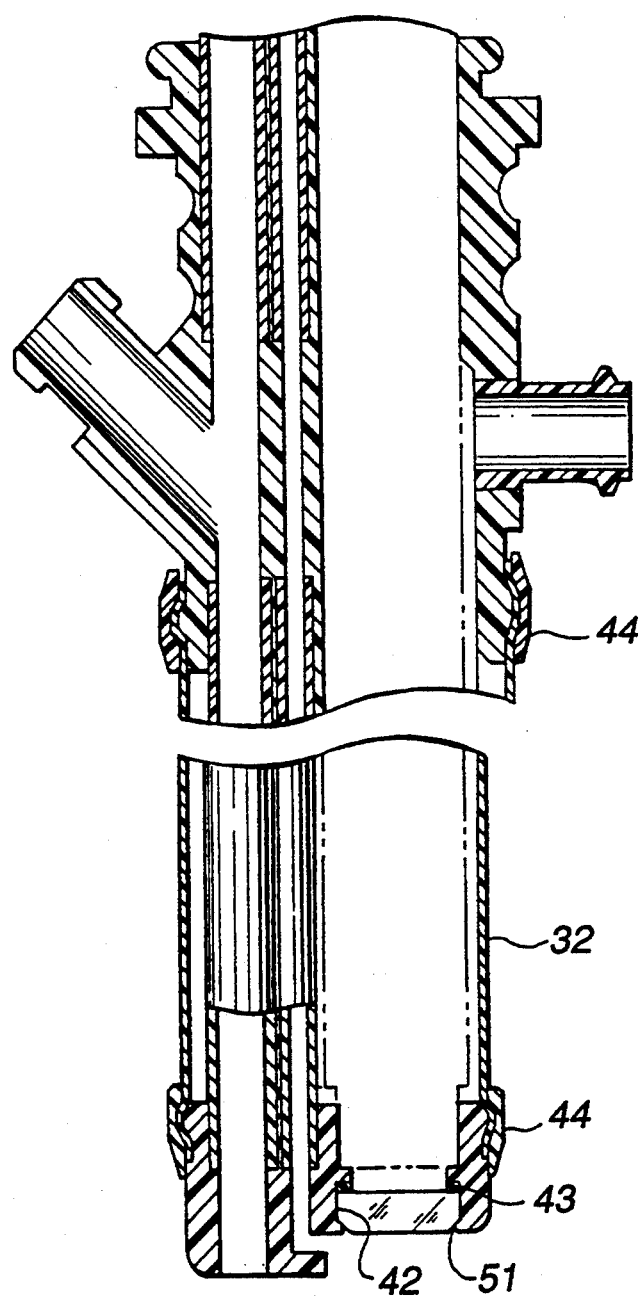

FIGS. 1 to 5 respectively illustrate a first embodiment of the present invention. FIG. 1 is a perspective view which illustrates the overall structure of an endoscope apparatus of a type having a cover for covering the endoscope. FIG. 2 is a side elevational view which illustrates the endoscope apparatus with a cover for covering the endoscope. FIG. 3 is a vertical cross sectional view which illustrates a cover of an insert of the cover for the endoscope in a state where it is fastened to the endoscope with the cover. FIG. 5 a vertical cross sectional view which illustrates a forceps cap which is fastened to a forceps insertion port at the time of use.

The endoscope apparatus according to the first embodiment incorporates a movable cart 1 on which the following units are mounted: a light source unit 2 including a light source for irradiating, for example, a subject of inspection, a video processor 3 for processing signals supplied from an imaging device (omitted from illustration), a fluid control unit 4 for controlling supply of air and water and the like, a cover expander (hereinafter abbreviated to an "expander") 5, and a monitor 6 for observing an image, and so forth. Furthermore, an endoscope 7 with the endoscope cover (hereinafter called an "endoscope with the cover"), that is, covered with the endoscope cover (hereinafter called the "cover") 10, is connected to the light source device 2.

The endoscope 7 with the cover 10 has, as shown in FIG. 2, an elongated insert 17 extending from a control unit 16 adjacent to an operator, and has a universal cord 18 extending from the side portion of the control unit 16. The insert 17 has a warping portion 46 and a leading portion 27 of the endoscope 7 with the cover 10, the warping portion 46 and the leading portion 27 being adjacently located similarly to those of the conventional endoscope. Thus, the endoscope 7 with the cover 10 can be warped by an angle knob 21 of the control unit 16 via a warping wire 47 (see FIG. 3) at the time of use in a state where the cover 10 is fastened. On the other hand, the universal cord 18 has a connector 18a disposed at the leading portion thereof, while having a cable 8 extending from the side portion thereof to be connected to the video processor 3 as shown in FIG. 1. As a result, an output signal from the imaging device (omitted from illustration) included in the leading potion 27 of the insert 17 is transmitted through the thus constituted passage to be received by the endoscope 7 with the cover 10. The control unit 16 has a holder 19 for holding the endoscope 7 adjacent to the leading portion of a control unit body 20, which includes the foregoing angle knob 21, an air/water-supply control switch 22, a suction control switch 23, and a function switch 24 for photographing, and the like. The angle knob 21 is arranged to be detachable from the control unit body 20. Also the angle knob 21 is so arranged that it is covered with an angle-knob cover 67 (see FIG. 19).

The cover 10 has the essential portion thereof consisting of the cover 11 for the insert 17, a cover 12 for the control unit 16 and the universal-cord cover 13 as shown in FIG. 1, disposed in this order when viewed from the leading portion. Then, the detailed description of the cover 11 for the insert 17 of the cover 10 will now be described with reference to FIGS. 3 and 4. It should be noted that the endoscope 7 with the cover 10 is covered with the cover 11 for the insert 17 in the manner in which the cover 11 for the insert 17 is held by a cover holder 15 (see FIG. 1).

As shown in FIG. 3, the cover 11 for the insert 17 has a 1 leading portion 25 of the cover 11 for the insert 17, an outer case 32 of the cover 11 for the insert 17, and an acceptor 36 for fixing the control unit 16 of the endoscope 7, disposed in the foregoing order when viewed from the leading portion of the apparatus.

A leading portion 25 of the cover 11 is mainly composed of a leading unit 26 made of polysulfone which is a thermoplastic resin. The leading unit 26 has an observation window 29 at a position corresponding to a portion outside an optical axis of an observation optical system 28 and an irradiation optical system 27a (see FIG. 13) disposed in a leading portion 27 of the endoscope 7 with the cover 10. The observation window 29 is a transparent window made of plastic such as polypropylene and received by the leading unit 27 via a rubber packing 43 made of silicon rubber. That is, the observation window 29 is urged outwards by the rubber packing 43 and its separation is prevented by a fastening portion 51 formed adjacent to the outer end surface of a fitting hole 42. The rubber packing 43 enables water-tightness to be achieved to prevent internal invasion of water or the like. Furthermore, the leading portion 25 of the cover 10 is provided with an air/water-supply nozzle 30 opened to face the observation window 29 to clean the observation window 29 and a forceps outlet port 31 through which a curing device is ejected.

The leading unit 26 described above hermetically receives the outer case 32 of the cover 11 for the insert 17 to insulate the insert 17 of the endoscope 7 with the cover 10 from the external environment, the outer case 32 being made of a thermohardening resin such as polyurethane. The outer case 32 is hermetically held and fixed by a fixing ring 44 made of a thermohardening resin such as an epoxy resin. The outer case 32 includes a suction tube 48 adjacent to insert 17 and communicated with the forceps outlet port 31, a tube-like air-supply passage 49 made of a resin and communicated with the air/water-supply nozzle 30, and a water-supply passage 50 adjacent to the insert, which are hermetically press-fitted and fixed into the leading unit 26. The foregoing passages.48, 49 and 50 are each made of a thermohardening resin such as polyurethane, while their other end portions are hermetically press-fitted and fixed into the acceptor 36 for fixing the control unit 16 of the endoscope 7 to be described later.

The outer case 32 of the cover 11 for the insert 17 has, at a position adjacent to the operator, the acceptor 36 for fixing the control unit 16 of the endoscope 7 and made of the same material as the leading unit 26, the acceptor 36 being also hermetically fixed by the fixing ring 44 made of a thermohardening resin such as an epoxy resin. The acceptor 36 for fixing the control unit 16 of the endoscope 7 is, as shown in the drawing, provided with a forceps insertion port 33 connected to the forceps outlet port 31, an expansion tube acceptor 34 for connecting the expansion tube 14 (see FIG. 1) extending from the expander 5, and a connection portion 35 to be connected to the holder 15 (see FIG. 1), and the like. Furthermore, the acceptor 36 for fixing the control unit 16 of the endoscope 7 has, at a position adjacent to the operator, an opening 38 of an endoscope insertion channel 37 formed in the outer case 32 of the cover 11 for the insert 17.

The acceptor 36 for fixing the control unit 16 of the endoscope 7 has, at a position adjacent to the operator, a suction passage 41, an air-supply passage 39 and a water-supply passage 40, respectively press-fitted and connected to the suction tube 48 adjacent to the insert, the air-supply passage 49 adjacent to the insert 17 and the water-supply passage 50 adjacent to the insert, and made of a thermohardening resin such as polyurethane. The other end portions of the foregoing passages 39, 40 and 41 passes through the cover 12 for the control unit 16, and the universal-cord cover 13 followed by respective connections to an air-supply source, a water-supply source and a suction source via a fluid control unit 56 of the fluid control unit 4.

The forceps insertion port 33 is arranged so that a forceps cap 52, as shown in FIG. 5, can be fastened to it. The forceps cap 52 is composed of a shell 53 made of a thermoplastic resin such as polyethylene and two valves disposed in the shell 53 and molded by rubber.

The cover 12 for the control unit 16 is made of a sheet made of a resin and formed into a substantially cylindrical shape, has an end portion fixed to the acceptor 36 for fixing the control unit 16 of the endoscope 7, and has another end portion fixed to the base portion of the universal cord 18. An arrangement is made such that the universal cord 18 is covered with the universal-cord cover 13. The angle knob 21 which is detachable from the cover 12 for the control unit 16, the universal-cord cover 13 and the control unit 16 are also made by molding a thermoplastic resin such as polyethylene or polypropylene.

It should be noted that the foregoing leading unit 26 and the acceptor 36 for fixing the control unit 16 of the endoscope 7 are made of the same material, that is polysulfone and the like which are thermoplastic resins which can be recycled. If an olefin resin such as polyethylene, polypropylene, or polybutylene is used as the foregoing thermoplastic resin, the recycling process can further easily be performed.

Furthermore, the foregoing structure is arranged in such a manner that all the elements made of different materials are fixed to each other by press fitting or fastening by using no adhesive agent at the time of connecting the members constituting the cover portion 11 for the insert 17, thus decomposition being enabled. Although the expansion tube acceptor 34 and the acceptor 36 for fixing the control unit 16 of the endoscope 7 are made of the same material, they are fixed to each other without using an adhesive agent.

The operation of the first embodiment as described above will now be described.

After the inspection by using the endoscope has been completed, the endoscope 7 with the cover 10 is removed from the cover 11 for the insert 17, and then the cover 11 for the insert 17 is subjected to a sterilization process by using autoclave or sterilizing gas. Then, the cover 11 for the insert 17 is decomposed to be divided.

Since the elements made of different materials are connected to each other by press fitting or fastening as described above, the decomposition can easily be performed. Although the acceptor 36 for fixing the control unit 16 of the endoscope 7 and the expansion tube acceptor 34 are independent members, they do not need to be decomposed because they are made of the same material (polysulfone) and no adhesive agent or the like is used.

Then, the members are divided into two groups composed of a group made of the thermohardening resin which cannot be recycled and a group made of the thermoplastic resin which can be recycled. The members of the group that cannot be recycled are: the members made of the polyurethane resin, that is, the outer case 32 of the cover 11 for the insert 17, the suction passage 41, the air-supply passage 39, the water-supply passage 40, the water-supply passage 50 adjacent to the insert 17, the air-supply passage 49 adjacent to the insert 17, and the suction tube 48 adjacent to the insert 17; and the fixing ring 44 which is made of the epoxy resin. The group that can be recycled are: the members made of the polysulfone resin, that is, the leading unit 26, and the acceptor 36 for fixing the control unit 16 of the endoscope 7; the observing window made of polypropylene; and the rubber packing 43. Furthermore, they are classified depending upon the material followed by collection with collection means such as a recycle box to be, as the recycle members, subjected to a recycle process.

Since the cover 12 for the control unit 16, the universal-cord cover 13, the angle-knob cover 67 (see FIG. 19) and the forceps cap 52 are made of the material which can be recycled, they are subject to the process similarly to the cover 11 for the insert 17.

According to the first embodiment as described above, the cover for the insert is a non-returnable member, but at least two main components are made of the same material which can be recycled, thus facilitating the division work at the time of the disposal process. As a result, a satisfactory contribution can be made to save the resources. Since no adhesive agent is used to connect the members made of different materials, the members can easily be decomposed and divided.

Figure 6:
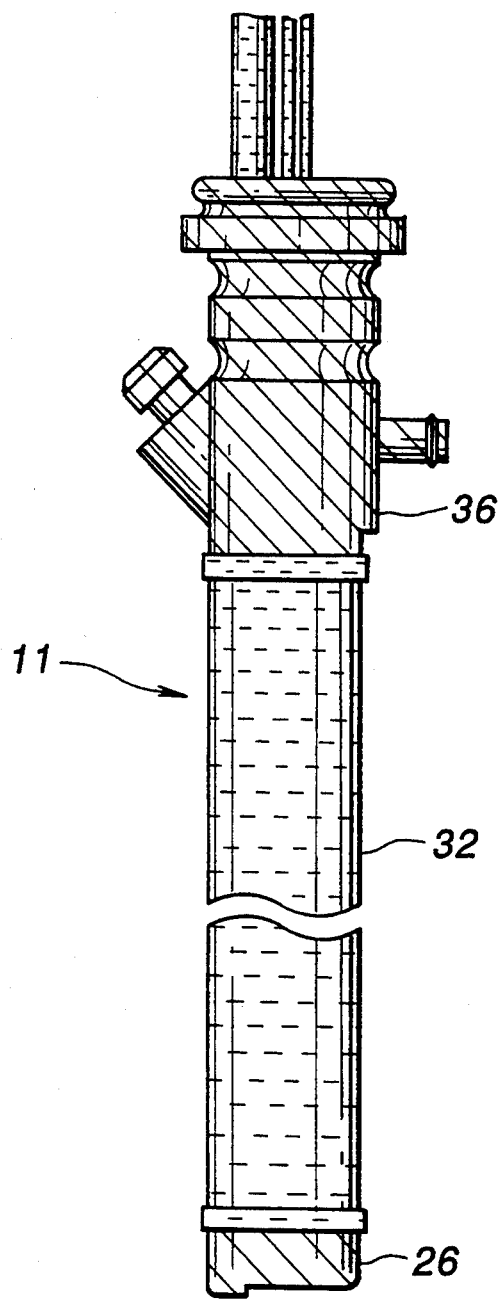
FIG. 6 is a side elevational view which illustrates a cover for an insert according to a second embodiment of the present invention.

FIG. 6 is a side elevational view which illustrates a cover for an insert according to a second embodiment of the present invention. Since the second embodiment is arranged similarly to the first embodiment, the descriptions will be made about only the different portions.

The leading unit 26 and the acceptor 36 for fixing the control unit of the endoscope are made of the same material which can be recycled (which can be regenerated) such as polypropylene. Furthermore, they are colored with green to indicate that they can be recycled, while the members that are not recycled, for example, the outer case 32 of the cover for the insert is colored with gray. More specifically, the members made of the same material are colored with the same color. The second embodiment exhibits substantially similar operation and effects to those of the first embodiment. Furthermore, an advantage can be realized in that the members, which can be recycled, can be immediately and visually recognized. Moreover, the members made of the same material which can be recycled are colored with the same color, resulting in the identification can be facilitated and the division can be facilitated assuredly.

Figure 7:
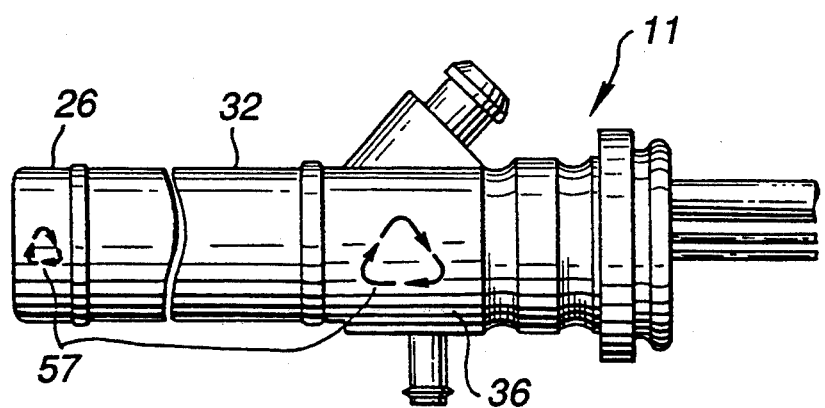
FIG. 7 is a side elevational view which illustrates an acceptor for fixing a control unit of the endoscope, which is a component of a cover for an insert, and a leading unit according to a third embodiment of the present invention.

FIG. 7 is a side elevational view which illustrates an acceptor 36 for fixing the control unit of the endoscope and a leading unit according to a third embodiment of the present invention. Since the third embodiment is arranged substantially similarly to the first and the second embodiments, the descriptions will be made about the different portions.

The acceptor 36 for fixing the control unit of the endoscope and the leading unit 26 have recycle marks 57 indicated thereon. Furthermore, the acceptor 36 for fixing the control unit of the endoscope and the leading unit 26 are made of the same material and able to be recycled similarly to the foregoing embodiments.

The operation and the effects of the third embodiment arranged as described above are substantially the same as those of the first and the second embodiments. Furthermore, an advantage can be attained in that the recycle marks enables the immediate visual recognition to be performed.

Figure 8:
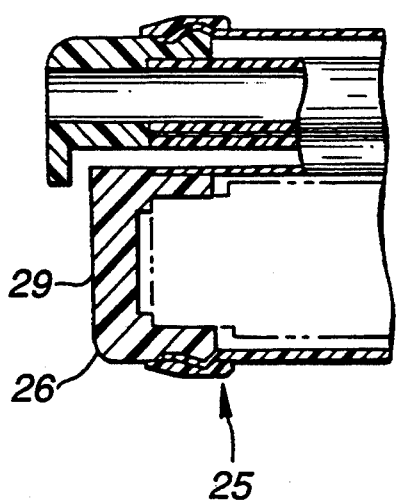
FIG. 8 is a cross sectional view which illustrates a leading unit of a cover for the insert according to a modification of the present invention.

The present invention is not limited to the foregoing embodiments. For example, an arrangement shown FIG. 8 which is a cross sectional view which illustrates the leading unit of the cover for the insert may be employed. In this case, the leading unit 26 and the observing window 29 may be integrally formed by using transparent plastic such as polypropylene which can be recycled in place of independently forming the foregoing members. Also in this case, at least two members such as the leading unit 26 and the acceptor 36 for fixing the control unit of the endoscope are made of the same material.

Although the foregoing embodiments have an arrangement in that the leading unit and the acceptor for fixing the control unit of the endoscope are made of the same material, all members forming the cover for the insert may, of course, be made of the same material which can be recycled. In this case, the necessity for decomposing and dividing the components at the time of the process can be eliminated. The materials which can be recycled may be selected from a thermoplastic resin group consisting of polyethylene, polypropylene, and polyester, and the like.

Figure 10:
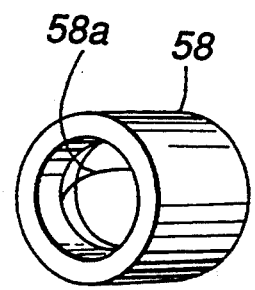
FIGS. 9 to 10 illustrate a fourth embodiment of the present invention, where
Figure 9:
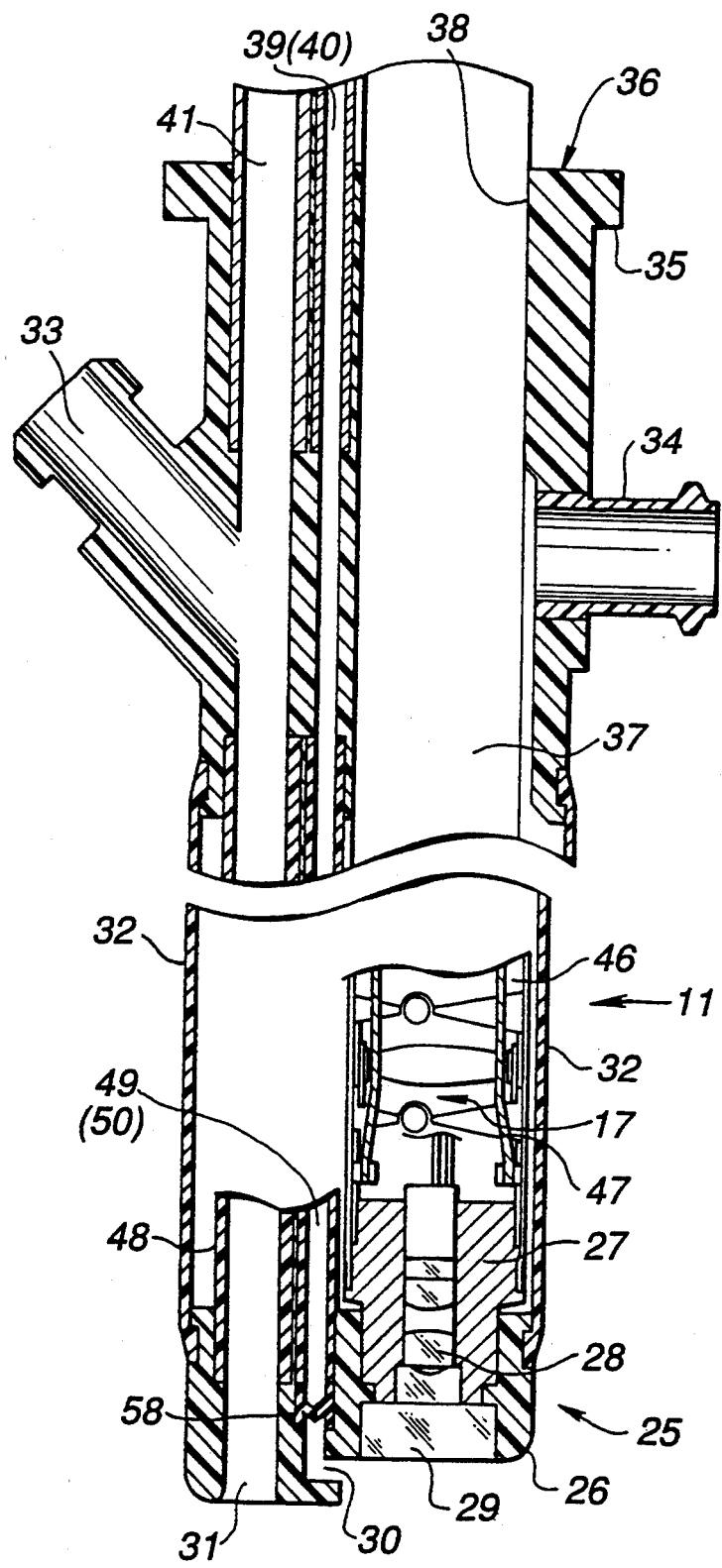

FIGS. 9 and 10 illustrate a fourth embodiment, in which FIG. 9 is a vertical cross sectional view which illustrates a cover for the insert of the endoscope in a state where it is fastened to the endoscope with the cover, and FIG. 10 is a perspective view which illustrates a check valve. Since the fourth embodiment is arranged substantially similarly to the first embodiment, the descriptions will be made about only the different portions.

The endoscope apparatus according to the fourth embodiment is shown in FIG. 1 and the endoscope 7 with the cover 10 is shown in FIG. 2.

The cover 11 for the insert 17 incorporates, as shown in FIG. 9, the leading portion 25 of the cover 11, the outer case 32 of the cover 11 for the insert 17, and the acceptor 36 for fixing the control unit 16 of the endoscope 7 disposed in the foregoing order when viewed from the leading portion.

The leading portion 25 of the cover 11 is mainly composed of a leading unit 26 made of a thermoplastic resin such as polyethylene. As shown in FIG. 9, the leading unit 26 has an observation window 29 at a position corresponding to a portion outside an optical axis of an observation optical system 28 and an irradiation optical system 27a (see FIG. 13) disposed in a leading portion 27 of the endoscope 7 with the cover 10. The observation window 29 is a transparent window made of a resin such as polypropylene and press fitted into the leading unit 26 to keep water tightness. Furthermore, the leading portion 25 of the cover 10 is provided with an air/water-supply nozzle 30 opened to face the observation window 29 to clean the observation window 29 and a forceps outlet port 31 through which a curing device is ejected.

The leading unit 26 as described above includes, by hermetically press-fitting, the suction tube 48 adjacent to the insert 17 communicated with the forceps outlet port 31, the air-supply passage 49 adjacent to the insert 17, communicated with the air/water-supply nozzle 30 and made of a resin tube, and the water-supply passage 50 adjacent to the insert 17. The passages 48, 49 and 50 are made of a thermoplastic resin such as polyethylene and have the other ends which are hermetically press-fitted into the acceptor 36 for fixing the control unit 16 of the endoscope 7.

The air-supply passage 49 adjacent to the insert 17, communicated with the air/water-supply nozzle 30 and made of a resin tube and/or the water-supply passage 50 has a check valve 58 disposed in the leading unit 26, the check valve 58 being integrally formed with an elastic material such as silicon rubber. The check valve 58 is formed into a cylindrical shape including a semispherical insulating wall which has cross slits 58a at the central portion thereof. As a result, backward flows of contaminants and mucus through the passages are prevented. Therefore, even if the cover 11 for the insert 17 is removed from the endoscope 7 after the inspection with the endoscope has been completed, dripping of mucus or the like from the passage can be prevented.

The outer case 32 of the cover 11 for the insert 17 has, at a position adjacent to the operator, the acceptor 36 for fixing the control unit 16 of the endoscope 7 and made of the same material as the leading unit 26, the acceptor 36 being made of a resin such as polyethylene and hermetically connected and fastened. The acceptor 36 for fixing the control unit 16 of the endoscope 7 is, as shown in the drawing, provided with a forceps insertion port 33 connected to the forceps outlet port 31, an expansion tube acceptor 34 made of a resin such as polyethylene for connecting the expansion tube 14 (see FIG. 1) extending from the expander 5, and a connection portion 35 to be connected to the holder 15 (see FIG. 1), and the like. Furthermore, the acceptor 36 for fixing the control unit 16 of the endoscope 7 has, at a position adjacent to the operator, an opening 38 of an endoscope insertion channel 37 formed in the outer case 32 of the cover 11 for the insert 17.

The acceptor 36 for fixing the control unit 16 of the endoscope 7 has, at a position adjacent to the operator, a suction passage 41, an air-supply passage 39 and a water-supply passage 40, respectively press-fitted and connected to the suction tube 48 adjacent to the insert, the air-supply passage 49 adjacent to the insert 17 and the water-supply passage 50 adjacent to the insert. The other end portions of the foregoing passages 39, 40 and 41 pass through the cover 12 for the control unit 16, and the universal-cord cover 13 followed by respective connections to an air-supply source, a water-supply source and a suction source via a fluid control unit 56 of the fluid control unit 4.

The cover 12 for the control unit 12 is made of a sheet formed of a resin and formed into a substantially cylindrical shape, and has an end portion fixed to the acceptor 36 for fixing the control unit 16 of the endoscope 7, and has another end portion fixed to the base portion of the universal cord 18. The arrangement is such that the universal cord 18 is covered with the universal-cord cover 13.

In the foregoing structure, all members constituting the cover 11 for the insert 17, that is, the following members are made of a combustible resin: the leading unit 26, the observation window 29, the outer case 32 of the cover 11 for the insert 17, the suction tube 48 adjacent to the insert 17, the air-supply passage 49 adjacent to the insert 17, the water-supply passage 50 adjacent to the insert 17, the acceptor 36 for fixing the control unit 16 of the endoscope 7, the acceptor 34 for connecting the expansion tube 14 press-fitted into the acceptor 36, and the check valve 58. The employed material does not generate poisonous gas such as chloride gas (for example, COC 12) at the time of the incineration process. It should be noted that that the leading unit and the acceptor for fixing the control unit of the endoscope are made of the same material as described above.

The cover 10 for the endoscope 7 is disposed as a combustible by removing the cover 11 for the insert 17 from the insert 17 after the inspection with the endoscope has been completed.

According to the fourth embodiment, the cover 11 for the insert 17 is fully made of the combustible resin, thus resulting in an effect to be obtained in that its components can be subjected-to the combustion process while eliminating the necessity for decomposing them. Furthermore, the generation of the poisonous gas at the time of the combustion process can be prevented. Moreover, an advantage can be obtained in that the material of the cover 11 for the insert 17 can be recycled as various purpose fuel resources.

Figure 11:
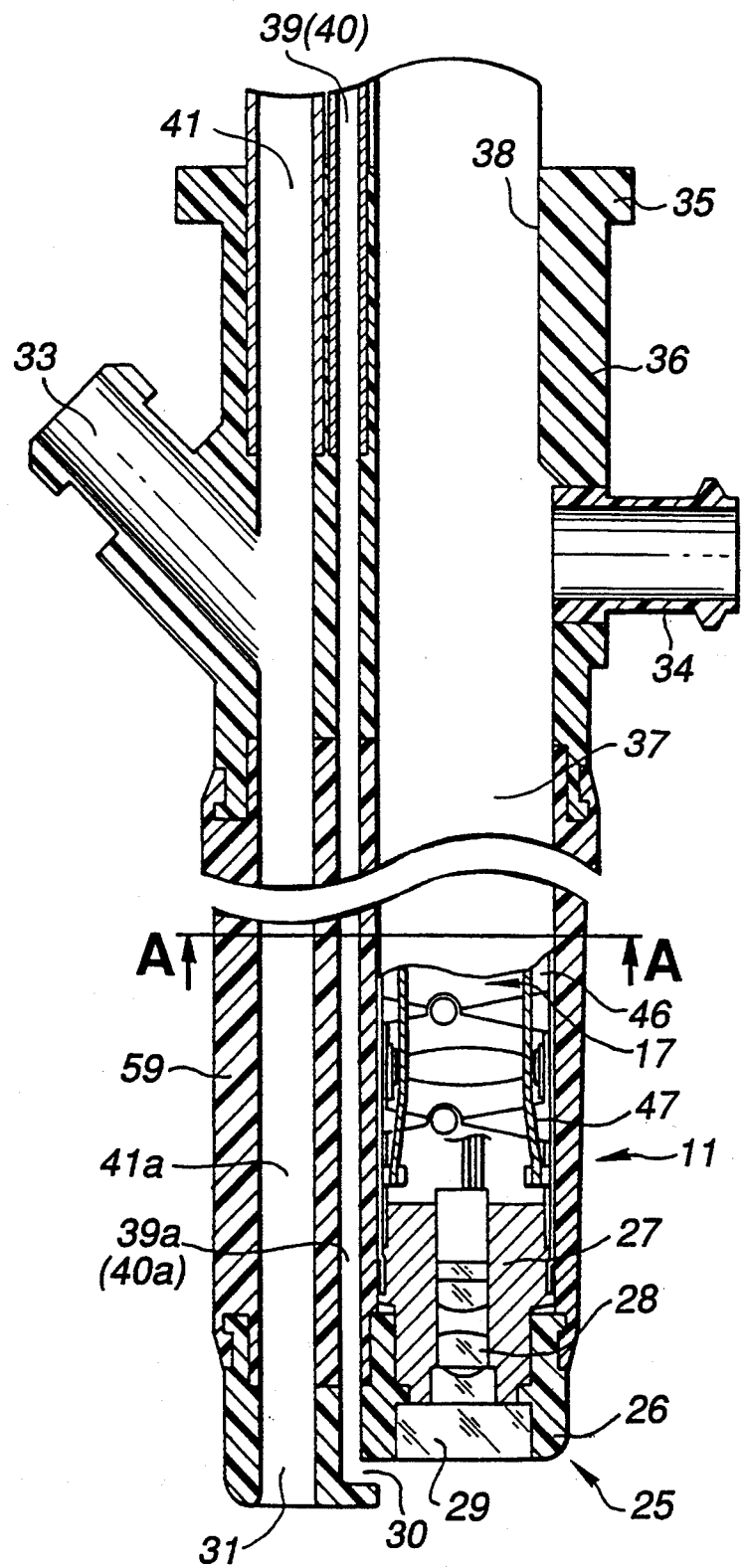
FIGS. 11 to 14 illustrate a fifth embodiment of the present invention, where
Figure 12:
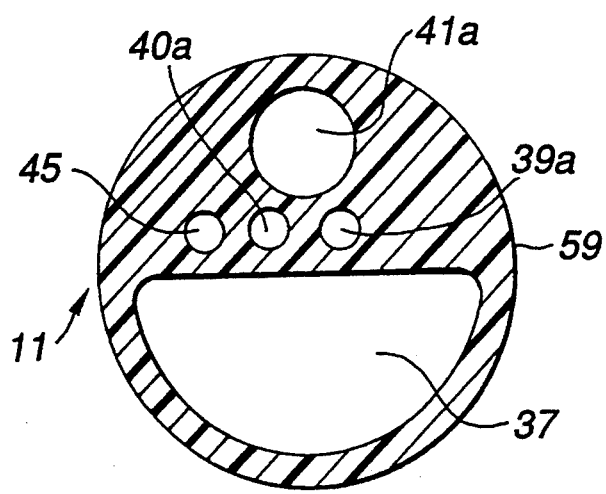
Figure 13:
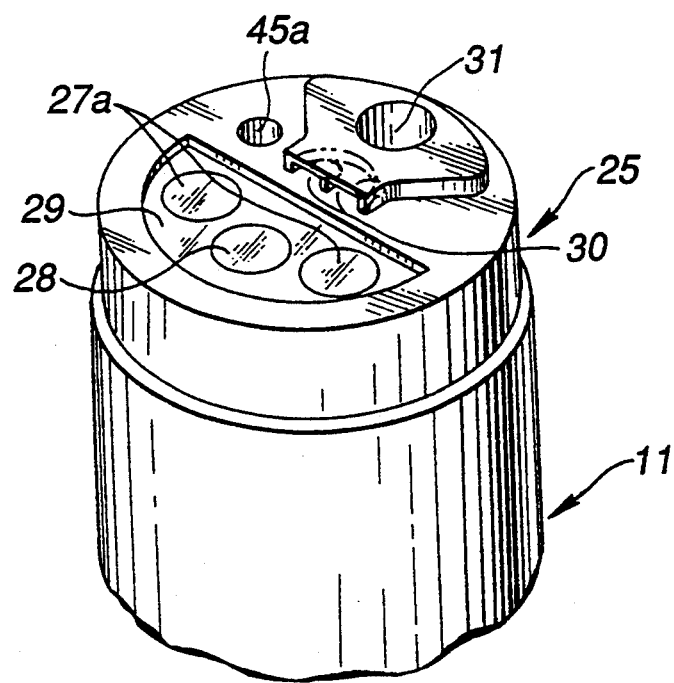
Figure 14:
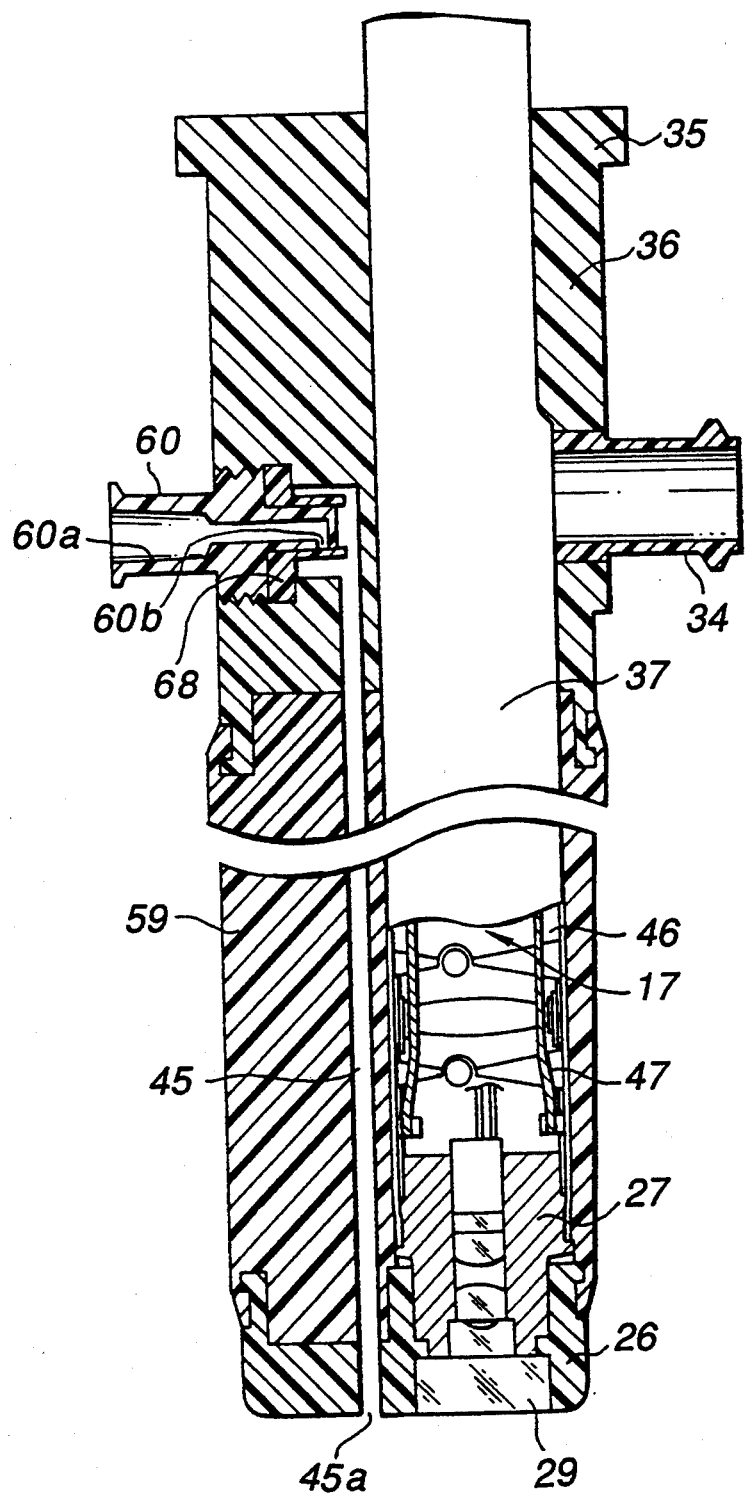

FIGS. 11 to 14 illustrate a fifth embodiment of the present invention, where FIG. 11 is a vertical cross sectional view which illustrates a cover for an insert of an endoscope in a state where it is fastened to the endoscope with the cover. FIG. 12 is a cross sectional view taken along line A—A of FIG. 11 which illustrates a multilumen tube in a state where the endoscope with the cover is not fastened. FIG. 13 is a perspective view which illustrates a perspective view which illustrates a leading portion of the insert to which the cover for the insert is fastened. FIG. 14 is a vertical cross sectional view which illustrates a cover for the insert of the endoscope in a state where it is fastened to the endoscope with the cover and in which a portion including the forward water-supply passage is shown. The same elements as those according to the fourth embodiment are omitted from the description, and only the different elements will now be described.

The fourth embodiment has the arrangement in which a suction tube 48 adjacent to the insert 17, the air-supply passage 49 adjacent to the insert 17, the water-supply passage 50 adjacent to the insert 17 in the outer case 32 of the cover 11 for the insert 17 are, as tubes, passed between the leading unit 26 and the acceptor 36 for fixing the control unit 16 of the endoscope 7. However, the fifth embodiment has an arrangement in which a suction tube 41a adjacent the insert, an air-supply passage 39a adjacent to the insert, a water-supply passage 40a adjacent to the insert and an endoscope insertion channel 37 are formed integrally with the outer case of the cover for the insert to form a multilumen tube 59.

The multilumen tube 59 is made of a polyester resin or the like, has an end portion fixed to the leading unit 26 made of polyethylene, and has another end portion fixed to the acceptor 36 for fixing the control unit 16 of the endoscope 7. The multilumen tube 59 has, as shown in FIG. 12, holes to serve as the suction tube 41a adjacent to the insert, the water-supply passage 40a adjacent to the insert, the air-supply passage 39a adjacent to the insert, the endoscope insertion channel 37, and the forward water-supply passage 45.

The leading portion 25 of the cover 11 of the insert 17 has, as shown in FIG. 13, a forward water-supply port 45a. The forward water-supply port 45a is, as shown in FIG. 14, communicated with the forward water-supply passage 45. The forward water-supply passage 45 is communicated with a water-supply accepter 60 fastened to the forward water-supply passage 45 by means of thread and made of polyethylene. The water-supply accepter 60 includes a lure lock 60a for an injector in the outer end portion thereof, and a hole communicated with this is bent sideward to become a side hole 60b. A valve 68 formed into a substantially cylindrical shape and made of silicon rubber or the like is fastened around the portion of the water-supply acceptor 60 adjacent to the leading portion to cover the foregoing side hole 60b. When water is supplied by an injector fastened to the water-supply acceptor 60, the valve 68 is deformed outwards so that water can be supplied through the side hole 60b. In an ordinary case, the side hole 60b is closed by the valve 68.

The observation window 29 is made of transparent polypropylene, as in the fourth embodiment, and is press-fitted and fixed to the leading unit 26.

All members forming the cover 11 of the insert 17 are made of combustible resin which does not generate at least chloride gas, similarly to as in the fourth embodiment.

According to the fifth embodiment described above, substantially similar operation and effects to those according to the fourth embodiment can be attained. Furthermore, the structure form by using the multilumen tube considerably facilitates the operation of assembling the cover for the endoscope at a low cost. Furthermore, the use of the multilumen tube prevents undesirable movement of each passage due to hydraulic pressure or atmospheric pressure. Moreover, the provision of the forward water-supply passage further widens the purposes of use in performing a curing operation.

Figure 15:
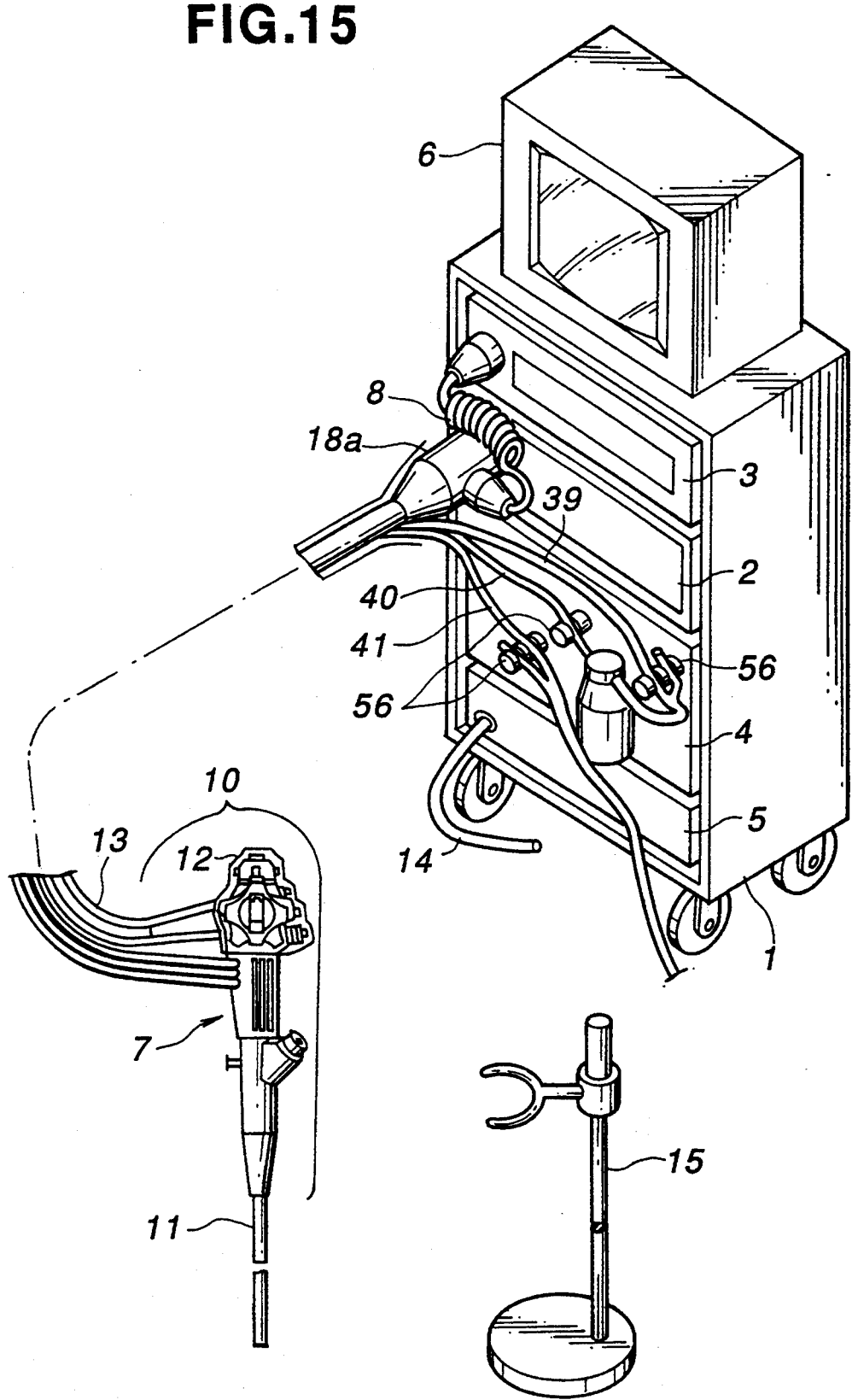
FIGS. 15 to 21 illustrate a sixth embodiment of the present invention, where
Figure 16:
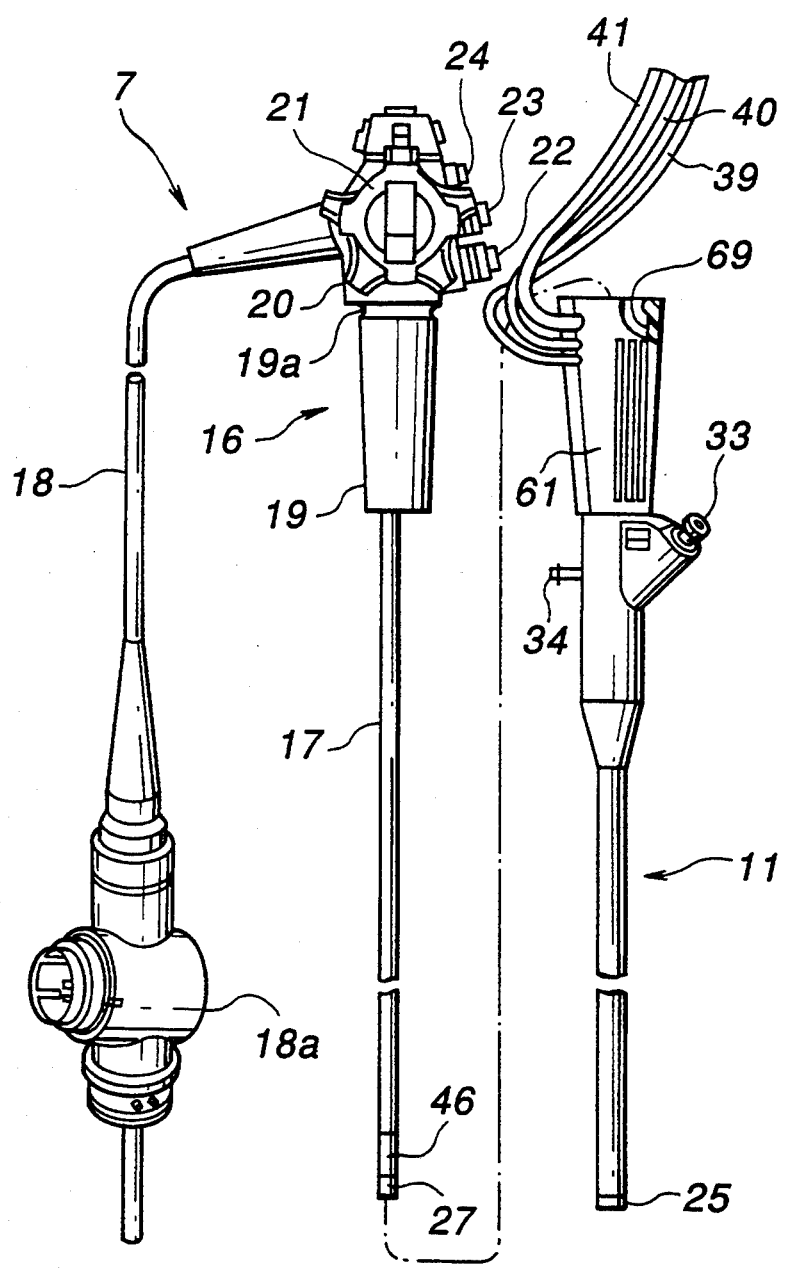
Figure 17:
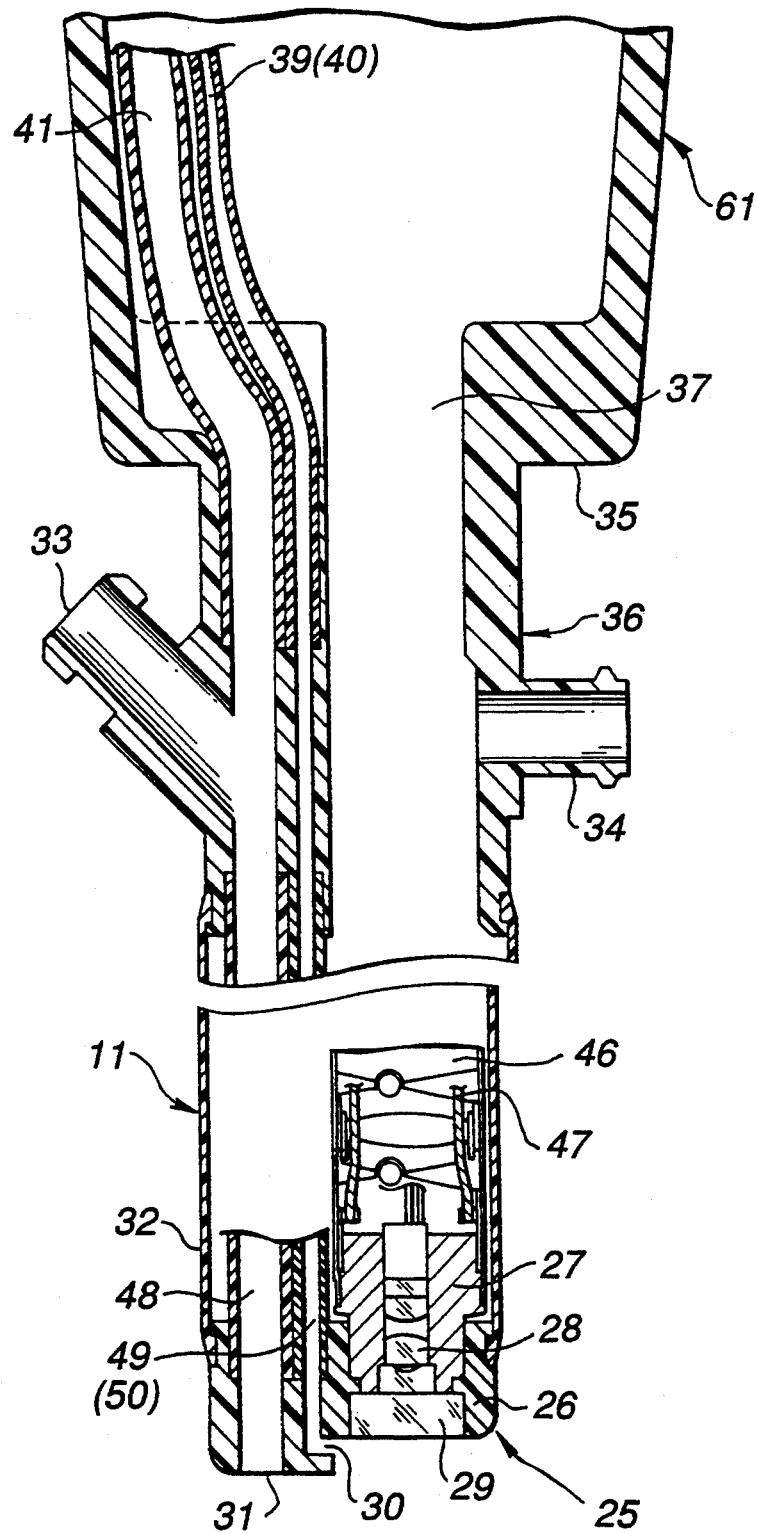
Figure 18:
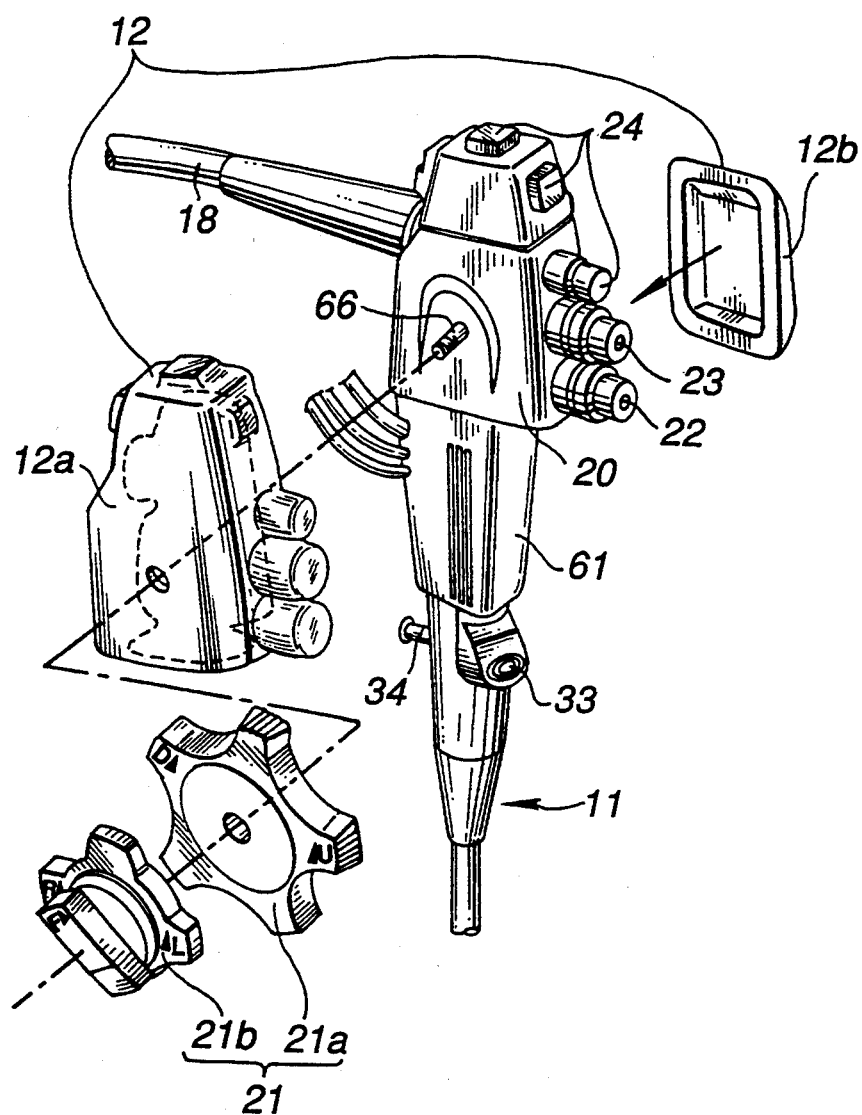
Figure 19:
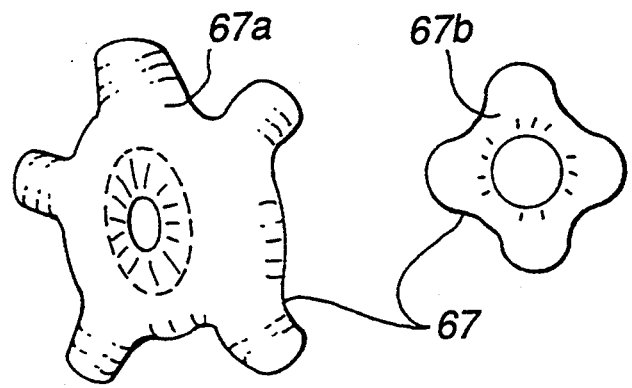
Figure 20:
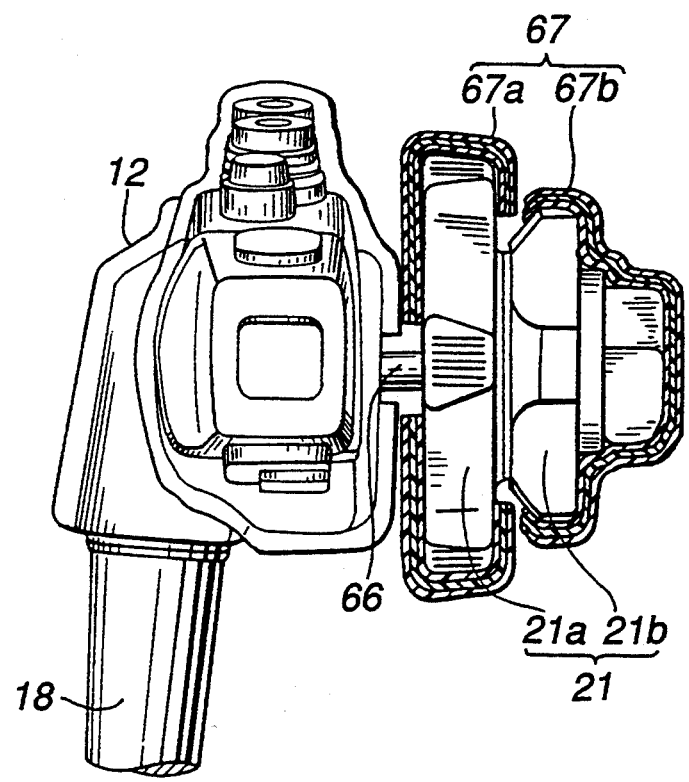
Figure 21:
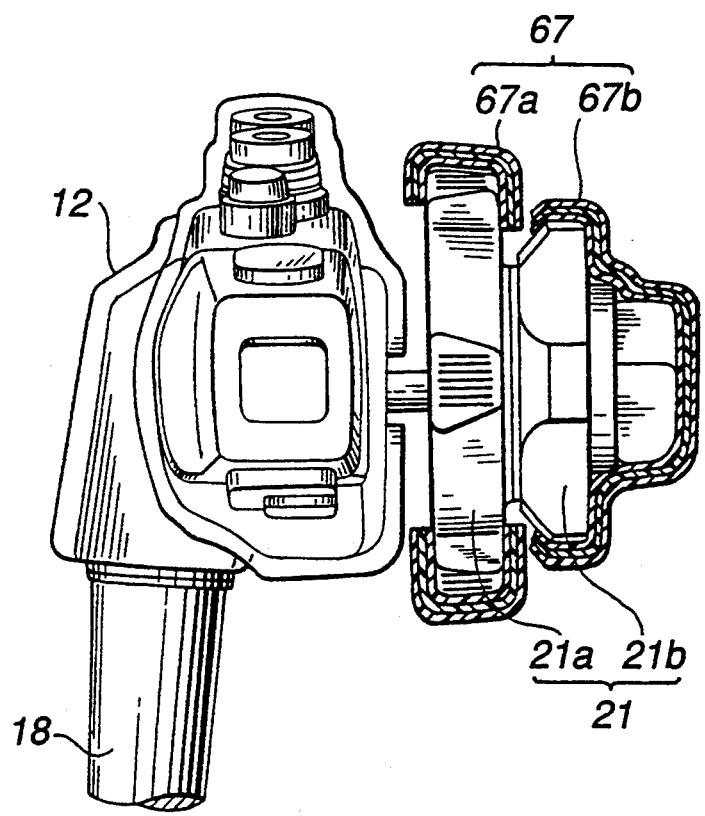

FIGS. 15 to 21 illustrate a sixth embodiment of the present invention, where FIG. 15 is a perspective view which illustrates the overall structure of the endoscope apparatus with the cover. FIG. 16 is a side elevational view which illustrates the endoscope with the cover and a cover of an insert of the endoscope. FIG. 17 is a vertical cross sectional view which illustrates the cover of the insert of the endoscope in a state where it is fastened to the endoscope with the cover. FIG. 18 is a perspective view which illustrates a state where a cover for the operation unit and an angle cover are fastened after the cover for the insert has been fastened to the endoscope with cover. FIG. 19 is a perspective view which illustrates the angle-knob cover. FIG. 20 is a plan view partially including a cross sectional view which illustrates the cover for the control unit, the angle knob and the angle-knob cover fastened to the body of the control unit. FIG. 21 is a plan view partially including a cross sectional view which illustrate another example of the angle-knob cover of the operation unit shown in FIG. 20. Since the sixth embodiment is arranged substantially similarly to the first embodiment, the description will be directed to different elements.

An endoscope apparatus according to this embodiment is arranged as shown in FIG. 15, and the endoscope 7 with the cover 10 is arranged as shown in FIG. 16 in a manner similar to the first embodiment.

The control unit 16 according to this embodiment has a holder 19 for holding the endoscope 7 adjacent to the leading portion of a control unit body 20. Furthermore, a fastening recess 19a is formed between them. The control unit body 20 has the angle knob 21, the air/water-supply control switch 22, the suction control switch 23 and a function switch 24 for photographing. The angle knob 21 is arranged to be detachable from the control unit body 20 similarly to each of the foregoing embodiments.

The cover 10 has the essential portion thereof consisting of the cover 11 for the insert 17, a cover 12 for the control unit 16 and the universal-cord cover 13, disposed as described above when viewed from the leading portion. The endoscope 7 with the cover 10 is so arranged that the cover 11 for the insert 17 is detachably fastened in a state where the cover 10 for the insert 17 is held by the cover holder 15 (see FIG. 15). The detailed structure of the cover 11 for the insert 17 of the cover 10 will now be described.

As shown in the drawings, the cover 11 for the insert 17 has, disposed in the following order when viewed from the leading portion, the leading portion 25 of the cover 11, the outer case 32 of the cover 11 for the insert 17, the acceptor 36 for fixing the control unit 16 of the endoscope 7, and a cover 61 for the holder 19.

The leading portion 25 of the cover 11 is mainly composed of the leading unit 26 made of polysulfone which is the thermoplastic resin. The leading unit 26 has an observation window 29 at a position corresponding to a portion outside an optical axis of an observation optical system 28 and an irradiation optical system 27a (see FIG. 13) disposed in a leading portion 27 of the endoscope 7 with the cover 10. The observation window 29 is a transparent window made of a resin and press-fitted to the leading unit 27. The leading portion 25 of the cover has an air/water-supply nozzle 30 opened to face the observation window 29 for cleaning the observation window 29 and a forceps outlet port 31 through which a curing device or the like is ejected.

The outer case 32 of the cover 11 for the insert 17 to insulate the insert 17 of the endoscope 7 with the cover 10 from the external environment and made of a thermoplastic resin is hermetically connected to the leading unit 26 constituted as described above. The outer case 32 of the cover 11 for the insert 17 includes a suction tube 48 adjacent to insert 17 and communicated with the forceps outlet port 31, a tube-like air-supply passage 49 communicated with the air/water-supply nozzle 30, and a water-supply passage 50 adjacent to the insert, which are hermetically press-fitted and fixed into the leading unit 26. The other end portions of the foregoing passages 48, 49 and 50 are hermetically press-fitted and fixed into the acceptor 36 for fixing the control unit 16 of the endoscope 7 to be described later.

The outer case 32 of the cover 11 for the insert 17 has, at a position adjacent to the operator, the acceptor 36 for fixing the control unit 16 of the endoscope 7 and made of the same material as the leading unit 26 such as polysulfone being hermetically fixed thereto. The acceptor 36 for fixing the control unit 16 of the endoscope 7 is, as shown in the drawing, provided with a forceps insertion port 33 connected to the forceps outlet port 31, an expansion tube acceptor 34 for connecting the expansion tube 14 (see FIG. 15) extending from the expander 5, and a connection portion 35 to be connected to the holder 15 (see FIG. 1), and the like. Furthermore, the endoscope insertion channel 37 formed in the outer case 32 of the cover 11 for the insert 17 is connected to the acceptor 36 for fixing the control unit 16 of the endoscope 7.

Furthermore, a holder cover 61 for covering the holder 19 of the endoscope with the cover is integrally and hermetically connected with the acceptor 36 for fixing the control unit 16 of the endoscope 7 at a position further adjacent to the operator than the acceptor 36 for fixing the control unit 16 of the endoscope 7. Also the holder cover 61 is made of polysulfone similarly to the leading unit 26. Moreover, a suction passage 41, an air-supply passage 39 and a water-supply passage 40, respectively connected to the suction tube 48 adjacent to the insert, the air-supply passage 49 adjacent to the insert 17 and the water-supply passage 50 adjacent to the insert, and made of a thermoplastic resin such as polyethylene are press-fitted and connected to positions more adjacent to the operator than the holder cover 61. The other end portions of the foregoing passages 39, 40 and 41 extend along the cover 12 for the control unit 16, and the universal-cord cover 13 followed by respective connections to an air-supply source, a water-supply source and a suction source via a fluid control unit 56 of the fluid control unit 4. Furthermore, the holder cover 61 has, in the inner surface at the rear end portion thereof, a fastening portion 69 so that it can be fastened and secured to the foregoing fastening recess 19a.

Then, the cover 12 for the control unit 16 is, as shown in FIG. 18, fastened to the endoscope 7 with the cover 10 to which the cover 11 for the insert 17 is fastened. Furthermore, the angle knob 21 is fastened to a knob shaft 66 projecting over a side surface of the control unit body 20.

The cover 12 for the control unit 16 is composed of a cover body 12a for the control unit 16 for covering various switches 22, 23 and 24 and the like, and a side member 12b of the cover 12 for the control unit 16 for covering the opposite side. The side member 12b of the cover 12 for the control unit 16 can be fixed to the cover body 12a for the control unit 16 by an adhesive tape or the like. After the cover 12 for the control unit 16 has been fastened, the angle knob 21 is fastened to the knob shaft 66. The angle knob 21 is composed of an angle knob 21a for up/down operation and an angle knob 21b for right/left operation. First, the up/down angle knob 21a is fastened, and then, the right/left operation angle knob 21b is fastened by means of thread.

The angle knob 21 fastened to the knob shaft 66 is covered with a bag-like angle-knob cover 67 having a shaft insertion hole therein as shown in FIG. 19. The angle-knob cover 67 is composed of up/down angle-knob cover 67a and a right/left operation angle-knob cover 67b provided to correspond to the up/down angle knob 21a and the right/left operation angle knob 21b. The foregoing angle-knob covers 67a and 67b are made of resin exhibiting excellent expansion characteristics so that the diameter of the shaft insertion hole can be made larger than the outer diameter of the angle knob 21 at the time of fastening.

When the endoscope is used, the angle knobs 67a and 67b are covered with one up/down angle-knob cover 67a and one right/left operation angle-knob cover 67b.

When one case has been completed, the used cover 67 is not removed but a new cover 67 is fastened. When all cases for a day have been completed, a plurality of the angle-knob covers 67 are collectively removed and disposed. As a result, a labor of removing the angle-knob cover 67 at each case can be eliminated. As an alternative to this, a plurality of angle-knob covers 67 are fastened to the angle knob 21 prior to performing the inspection as shown in FIG. 20 to remove the outermost angle-knob cover 67 after one case has been completed. As a result, a necessity of fastening the angle-knob cover 67 after each case has been completed can be eliminated.

Since the angle-knob cover 67 expands considerably, only one size is required to correspond to the angle knobs of a variety of sizes. A plurality of sizes of the angle-knob covers may be provided to correspond to the sizes of the angle knobs 21 by making the angle-knob covers 67 by a resin having poor expansion characteristics as shown in FIG. 21. In this case, the shaft insertion hole becomes somewhat larger than that in the foregoing case because the material has poor expansion characteristics.

It should be noted that the cover 11 for the insert 17, the cover 12 for the control unit 16, the universal-cord cover 13 and the angle-knob cover 67 are, of course, sterilized.

When the endoscope 7 with the cover according to the sixth embodiment is used, the cover 11 for the insert 17 is fastened to the insert 17 in the following manner that the holder of the control unit is covered with the holder cover 61.

According to the sixth embodiment described above, the suction passage 41, the air-supply passage 39 and the water-supply passage 40 are projected outwards at the holder of the control unit adjacent to the operator. Therefore, the extending tubes do not interrupt the handling, resulting in that the operation can easily be performed. Furthermore, the cover for the insert integrally cover the holder, thus resulting in no connection portion to be present below the holder that can easily be contaminated. Therefore, a necessity of taking care to prevent the invasion of contamination can be eliminated. In addition, the cover for the control unit does not move undesirably to form a gap, thus preventing contamination. Moreover, the structure is so arranged that the cover for the insert covers the holder, an advantage can be obtained in that the structure of the cover for the control unit can be simplified.

Figure 22:
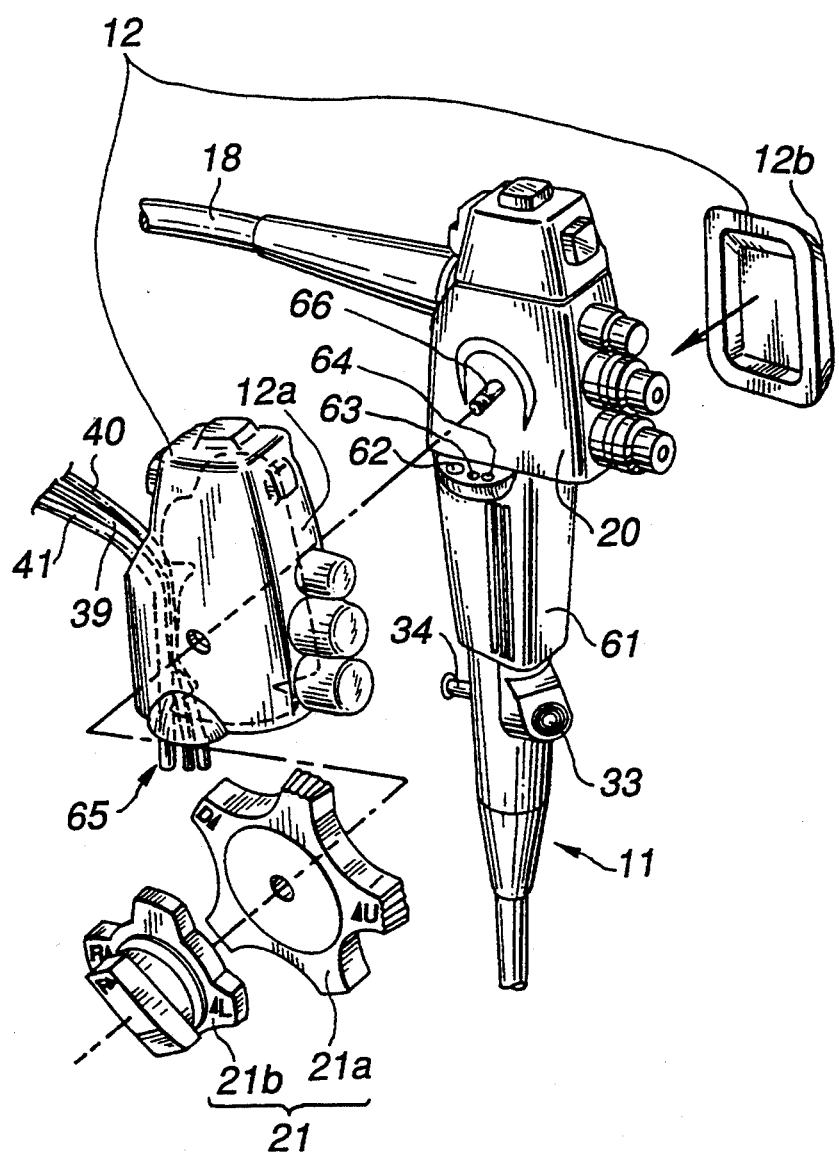
FIG. 22 is a perspective view which illustrates a state where the cover for the control unit and the angle knob are fastened after the cover for the insert has been fastened to the endoscope with the endoscope cover.

FIG. 22 is a perspective view which illustrates a seventh embodiment of the present invention, in which a state where a cover for the insert is fastened to the endoscope with the cover, and then a cover for the control unit and an angle knob are fastened. Since the seventh embodiment is arranged similarly to the sixth embodiment, only different portions will be described.

As contrasted with the sixth embodiment in which the suction passage 41, the air-supply passage 39 and the water-supply passage 40 extend over the position adjacent to the rear end of the cover 61 for the holder, the seventh embodiment has an arrangement in which each passage temporarily ends at the position adjacent to the rear end of the cover 61 for the holder, and a suction passage hole 62, an air-supply passage hole 63 and a water-supply passage hole 64 are opened. On the other hand, the cover 12 for the control unit has a connector 65 hermetically detachable to the passage holes 62, 63 and 64. The suction passage 41, the air-supply passage 39 and the water-supply passage 40 are inserted into the connector 65. The foregoing passages 39, 40 and 41 pass through the cover 12 for the control unit to extend outwards over the position adjacent to the rear end.

The operation of the seventh embodiment is substantially similar to that of the sixth embodiment but the cover 11 for the insert is fastened, and then the cover 12 for the control unit is fastened in the following manner such that the connector 65 is connected to respectively connect the suction passage hole 62 and the suction passage 41, the air-supply passage hole 63 and the air-supply passage 39, and the water-supply passage hole 64 and the water-supply passage 40.

According to the seventh embodiment described above, an effect similar to that of the sixth embodiment can be obtained. Furthermore, the suction, air-supply and the water-supply passages extend outwards at a position further adjacent to the operator than the position employed in the sixth embodiment, thus resulting in a fact that the foregoing passages do not interrupt the operation. As a result, the operation can further easily be performed.

In this invention, it is apparent that working modes different in a wide range can be formed on this basis of this invention without departing from the spirit and scope of the invention. This invention is not restricted by any specific embodiment except being limited by the appended claims.

What is claimed is:

1. An endoscope apparatus of a type including a cover for covering an endoscope comprising:
   a cover for an insert including at least two members which are made of different materials and are mutually connected with detachable connections,
   wherein at least one of said detachable connections is a press-fitting connection, and
   wherein said members forming said cover for said insert include at least two members among a leading unit, an acceptor for fixedly attaching a control unit of said endoscope to said cover for said insert, an outer case of a cover for said insert and a passage tube.

2. An endoscope apparatus of a type including a cover for covering an endoscope comprising:
   a cover for an insert including at least two members which are made of different materials and are mutually connected with detachable connections,
   wherein at least one of said detachable connections is a fastening connection; and
   wherein said members forming said cover for said insert include at least two members among a leading unit, an acceptor for fixedly attaching a control unit of said endoscope to said cover for said insert, an outer case of a cover for said insert and a passage tube.

3. An endoscope apparatus of a type having a cover for covering an endoscope comprising:
   an endoscope having a control unit including a handle at a leading portion of the body of said control unit and an elongated insert extending from said control unit; and
   an endoscope cover having a first cover for preventing said control unit of said endoscope from being polluted, and a second cover for an insert for integrally and completely covering and sealing said insert of said endoscope and said handle located on said body of said control unit, wherein said second cover for said insert has at least one fluid passage, and said fluid passage reaches a position adjacent to an operator in a portion covering said handle of said cover for said insert, and extends outwards.

4. An endoscope apparatus of a type having a cover for covering an endoscope comprising:

an endoscope having a control unit including a handle at a leading portion of the body of said control unit and an elongated insert extending from said control unit; and an endoscope cover having a first cover for preventing said control unit of said endoscope from being polluted, and a second cover for an insert for integrally and completely covering and sealing said insert of said endoscope and said handle located on said body of said control unit, wherein said second cover for said insert has at least one fluid passage, said fluid passage has an opening at a position adjacent to an operator in a portion covering said handle of said second cover for said insert, said first cover for said control unit has a fluid passage outwards extending from a position adjacent to an operator, and a connector connected to said opening with which said fluid passage is communicated.

5. An endoscope apparatus of a type having an endoscope cover for covering an endoscope comprising:

an endoscope with an endoscope cover having an elongated insert extending from a control unit having an angle knob;

angle-knob covers each distinct and separate from said endoscope cover for covering the surface of said angle knob and arranged in such a manner that a plurality of said angle-knob covers can be stacked at the time of fastening to said surface of said angle knob; and an endoscope cover having said angle-knob covers and covering at least the surface of said insert.

6. An endoscope apparatus of a type having an endoscope cover for covering an endoscope according to claim 5, wherein said angle-knob cover is not removed from said angle knob after each case has been completed, another angle-knob cover is used to cover the former angle-knob cover at the next case, and said angle-knob covers are simultaneously removed after a plurality of cases have been completed by the number corresponding to the number of cases.

7. An endoscope apparatus of a type having cover for covering an endoscope according to claim 5, wherein a plurality of said angle-knob covers are used to cover said angle knob prior to using said endoscope, and one angle-knob cover is removed after one case has been completed.

* * * * *